United States Patent
Jensen et al.

(10) Patent No.: US 12,180,457 B2
(45) Date of Patent: Dec. 31, 2024

(54) CLOSED-SYSTEM MANUFACTURING PROCESS FOR CAR-T CELLS

(71) Applicant: Seattle Children's Hospital, Seattle, WA (US)

(72) Inventors: Michael C. Jensen, Bainbridge Island, WA (US); Joshua Gustafson, Seattle, WA (US)

(73) Assignee: Seattle Children's Hospital, Seattle, WA (US)

( * ) Notice: Subject to any disclaimer, the term of this patent is extended or adjusted under 35 U.S.C. 154(b) by 1030 days.

(21) Appl. No.: 16/965,964

(22) PCT Filed: Feb. 4, 2019

(86) PCT No.: PCT/US2019/016497
§ 371 (c)(1),
(2) Date: Jul. 29, 2020

(87) PCT Pub. No.: WO2019/156926
PCT Pub. Date: Aug. 15, 2019

(65) Prior Publication Data
US 2021/0040448 A1 Feb. 11, 2021

Related U.S. Application Data

(60) Provisional application No. 62/627,129, filed on Feb. 6, 2018.

(51) Int. Cl.
*C12N 5/0783* (2010.01)
*A61K 39/00* (2006.01)

(52) U.S. Cl.
CPC ........ *C12N 5/0636* (2013.01); *A61K 39/4611* (2023.05); *A61K 39/4631* (2023.05); *A61K 39/464* (2023.05)

(58) Field of Classification Search
CPC ... C12N 5/0636; C12N 2510/00; A61K 35/17
See application file for complete search history.

(56) References Cited

U.S. PATENT DOCUMENTS

2014/0212398 A1* 7/2014 Reisner .............. A61K 39/461 435/325
2014/0271635 A1 9/2014 Brogdon et al.

FOREIGN PATENT DOCUMENTS

WO WO 2012/129514 A1 9/2012
WO WO2015162211 * 10/2015 ............ C12N 5/00
WO WO2018136566 * 1/2018 ........... C12N 5/0783

OTHER PUBLICATIONS

Mock et al. Automated manufacturing of chimeric antigen receptor T cells for adoptive immunotherapy using CliniMACS Prodigy. Cytotherapy, 18,1002-1011, 2016. (Year: 2016).*
Wang et al. Clinical manufacturing of CAR T cells: foundation of a promising therapy. Molecular Therapy—Oncolytics 3, 16015, 2016. (Year: 2016).*
Kaiser et al. Towards a commercial process for the manufacture of genetically modified T cells for therapy. Cancer Gene Therapy 22, 72-78, 2015. (Year: 2015).*
Zhu et al. Closed-system manufacturing of CD19 and dual-targeted CD20/19 chimeric antigen receptor T cells using the CliniMACS Prodigy device at an academic medical center. Cytotherapy, 20, 394-406, 2018. (Year: 2018).*
Anonymous. TexMACS. Immune cell culture media https://www.miltenyibiotec.com/us-en/products/texmacs-gmp-medium.html#170-076-306 (Year: 2016).*
Anonymous GRex Brochure 2016 https://www.wilsonwolf.com/wp-content/uploads/2016/11/. (Year: 2016).*
Gardner et al., Nov. 29, 2018, Early clinical experience of CD19 x CD22 dual specific CAR T cells for enhanced anti-leukemic targeting of acute lymphoblastic leukemia, Blood, 132(Suppl 1):278.
Jin et al., 2018, Enhanced clinical-scale manufacturing of TCR transduced T-cells using closed culture system modules, Journal of Translational Medicine, 16(1):1-13.
Lock et al., 2017, Automated manufacturing of potent CD20-directed chimeric antigen receptor T cells for clinical use, Human Gene Therapy, 28(10):914-925.
Turtle et al., Jun. 2016, CD19 CAR-T cells of defined $CD4^+:CD8^+$ composition in adult B cell ALL patients, J. Cl. Investigation, 126(6):2123-2138.
Lamers, Cor H.J et al., "T Cell Receptor-Engineered T Cells to Treat Solid Tumors: T Cell Processing Toward Optimal T Cell Fitness" Human Gene Therapy Methods, Dec. 2014, pp. 345-357, vol. 25.
Sommermeyer, Daniel et al., "Chimeric antigen receptor-modified T cells derived from defined CD8+ and CD4+ subsets confer superior antitumor reactivity in vivo" Leukemia, Feb. 2016, pp. 492-500, vol. 30, No. 2.
Xu, Yang et al., "Closely related T-memory stem cells correlate with in vivo expansion of CAR.CD19-T cells and are preserved by IL-7 and IL-15" Blood, Jun. 2014, pp. 3750-3759, vol. 123, No. 24.
Xu, Xiao-Jun et al., "Multiparameter comparative analysis reveals differential impacts of various cytokines on CART cell phenotype and function ex vivo and in vivo" Oncotarget, 2016, pp. 82354-82368, vol. 7, No. 5.
International Search Report for PCT/US2019/016497 dated Apr. 15, 2019.

* cited by examiner

*Primary Examiner* — Elly-Gerald Stoica
(74) *Attorney, Agent, or Firm* — Knobbe, Martens, Olson & Bear LLP

(57) ABSTRACT

Some embodiments provided herein relate to methods and compositions for making genetically modified T cells. In some such embodiments, CD4+ and CD8+ T cells are cultured in a single serum-free volume. In some embodiments, co-cultured CD4+ and CD8+ T cells can be transduced with a lentiviral vector, and a population of transduced T cells can be harvested within a shorter period of time than other conventional methods.

12 Claims, 2 Drawing Sheets

CLOSED-SYSTEM MANUFACTURING PROCESS FOR CAR-T CELLS

RELATED APPLICATION

This application is a U.S. National Phase Application of PCT International Application Number PCT/US2019/016497, filed on Feb. 4, 2019, designating the United States of America and published in the English language, which is an International Application of and claims the benefit of priority to U.S. Provisional Application No. 62/627,129, filed on Feb. 6, 2018. The disclosures of the above-referenced applications are hereby expressly incorporated by reference in their entireties.

FIELD OF THE INVENTION

Some embodiments provided herein relate to methods and compositions for making genetically modified T cells. In some such embodiments, CD4+ and CD8+ T cells are cultured in a single serum-free volume. In some embodiments, co-cultured CD4+ and CD8+ T cells are transduced with a lentiviral vector, and a population of transduced T cells are harvested within a shorter period of time as compared to conventional methods.

BACKGROUND OF THE INVENTION

Genetic modification of cells has been used in numerous fields such as research, medicine, industrial biotechnology and agriculture. There are several available techniques, for inserting a gene into a host genome. For example, a nucleic acid may be injected through a cell's nuclear envelope directly into the nucleus or administered to a cell using viral vectors to produce genetically modified cells.

Transfection with a viral vector is a common technique for producing genetically modified cells, such as T cells, in a technique known as viral transduction. The nucleic acid is introduced into the cells using a virus as a carrier, such as a lentivirus or adenovirus.

Viral transduction may be used to insert or modify genes in cells, such as mammalian cells using a plasmid. The plasmid used in viral transduction contains the genes to be transferred flanked by viral sequences that are used by viral proteins to recognize and package the viral genome into viral particles. This plasmid is inserted into the cell together with other DNA constructs that may carry viral genes required for formation of infectious virions. The viral proteins expressed by these packaging constructs may bind the sequences on the DNA/RNA that are to be transferred and inserted into viral particles. Typically, for safety reasons, none of the plasmids used contains all the sequences required for virus formation, so that simultaneous transfection of multiple plasmids is required to get infectious virions. Moreover, only the plasmid carrying the sequences to be transferred contains signals that allow the genetic materials to be packaged in virions, so that none of the genes encoding viral proteins are packaged. Viruses collected from these cells are then applied to the cells to be altered. The initial stages of these infections mimic infection with natural viruses and lead to expression of the genes transferred and (in the case of lentivirus/retrovirus vectors) insertion of the DNA to be transferred into the cellular genome. However, since the transferred genetic material does not encode any of the viral genes, these infections do not generate new viruses.

SUMMARY OF THE INVENTION

Some embodiments described herein relate to processes for making lentiviral modified T cells with minimal physical manipulation and within a shorter timeframe than conventional approaches. In some embodiments, CD4 and CD8 subsets of T-cells are placed in a co-culture in a unique media composition made from a base media, a protein supplement, and a cytokine cocktail. Lentivirus modification can also be performed in this system by magnetically concentrating the T-cells and incubating a transduction mixture with the cells for a defined or selected time in situ.

Some embodiments of the methods and compositions provided herein include a method of manufacturing genetically modified T cells. In some embodiments, the genetically modified T cells comprise a chimeric antigen receptor (CAR). Some such methods can include providing $CD8^+$ T cells and $CD4^+$ T cells in a first media in a single culture vessel, placing a second media into the single culture vessel, thereby producing co-cultured $CD4^+$ T cells and $CD8^+$ T cells, which are initiated for transduction, harvesting the initiated $CD4^+$ T cells and $CD8^+$ T cells; and transducing the initiated $CD4^+$ T cells and $CD8^+$ T cells with a vector, thereby producing genetically modified T cells. In some embodiments, i.e., optionally, the method is performed in a biological safety cabinet (BSC) and in some instances the vector is a viral vector. In some embodiments, the method is performed outside of a biological safety cabinet (BSC). In some alternatives, the vector is a lentiviral vector, adeno-associated vector or an adenoviral vector. Preferably, the transduction is performed by magnetically concentrating the initiated CD4+ T cells and CD8+ T cells, for example on CTS Dynabeads CD3/CD28, and incubating a transduction mixture with the initiated CD4+ T cells and CD8+ T cells for a defined period. In some alternatives, the culture media is removed from the culture vessel prior to adding the transduction media to the cells. In some alternatives, the defined period is in a range from about 1 hour to about 24 hours, from about 2 hours to about 12 hours, or from about 2 hours to about 5 hours. In some alternatives, the removed culture media is re-introduced into the vessel at the end of the defined period. In some alternatives, the transduction mixture comprises the vector. In these methods, the first media is, preferably, a cytokine free media and the second media, preferably, comprises at least one cytokine (e.g., IL-2, IL-7, IL-15, or IL-21 or any combination thereof). In some instances, the at least one cytokine is IL-15, IL-21 or IL-7. Preferably in these methods, the transducing step is performed 24 hours after the initiation step of the initiated CD4+ T cells and CD8+ T cells. In some alternative approaches, the first and or second media further comprises a protein supplement and, in some instances, the transduction mixture further comprises protamine sulfate or an interleukin or both. In some alternatives, the transduction mixture further comprises protamine sulfate or polybrene or both. In some alternatives, the transduction mixture comprises IL-2, IL-21, IL-15 or IL-7 or any combination thereof. Preferably, by using these methods, the genetically modified CD4+ T cells and CD8+ T cells are harvested the genetically modified $CD4^+$ T cells and $CD8^+$ T cells are harvested 3, 4, 5, 6, 7, 8, 9, 10, 11, 12, 13, or 14 days after the transducing step or any number of days within a range defined by any two aforementioned time periods. In some alternatives, the vector comprises a nucleic acid encoding a protein for therapy and the protein for therapy, desirably, comprises cytokines, chimeric cytokine/costimulatory proteins, pro- or anti-inflammatory proteins. Preferably in these methods, the vector comprises a nucleic acid encoding a chimeric antigen receptor and in some alternatives, the initiated CD4+ T cells and CD8+ T cells are further modified with a nuclease. In some such methods, the nuclease is a zinc finger nucleases (ZFNs), Transcription Activator-like Effector Nucleases (TALENs), the CRISPR/Cas system, RNA guided endonucleases or engineered meganuclease re-engineered homing endonucleases. Additionally, in some instances, the chimeric antigen receptor comprises a signal peptide, an antigen-binding domain, a transmembrane domain, a co-stimulatory domain, or an intracellular domain of a T-cell receptor or all of these domains. Preferably, these methods produce genetically modified T cells that express a chimeric antigen receptor (CAR), such as a CAR specific for binding or interaction with CD19, and by some approaches the vector further comprises a second nucleic acid encoding a genetic tag (e.g., EGFRt). In some alternatives, the process of manufacturing genetically modified T cells, such as CD4 and CD8 T cells within a single vessel may be performed in 3, 4, 5, 6, 7, 8, 9, 10, 11, 12, 13 or 14 days or for a time that is within a range of time defined by any two of the aforementioned time periods. In some alternatives, the at least one cytokine is IL-7, IL-15, or IL-21. In some alternatives, the at least one cytokine is IL-2, IL-7, IL-15, or IL-21.

In a second aspect, a method of manufacturing genetically modified T cells, wherein the genetically modified T cells comprise a chimeric antigen receptor is provided. The method comprises: a) providing CD8+ T cells and CD4+ T cells within two separate fractions of a first media, b) providing at least one cytokine into the separate fractions of first media, wherein the separate fractions comprises CD8+ T cells in a first fraction and CD4+ T cells in a second fraction, c) combining the first fraction and second fraction containing the CD8+ T cells and CD4+ T cells, thereby producing a combined cell fraction., d) providing Dynabeads (e.g., CTS Dynabeads CD3/CD28) to the combined cell fraction and magnetically concentrating the CD4+ T cells and CD8+ T cells, e) removing the Dynabeads, f) adding the combined cell fraction comprising the CD4+ and CD8+ cells into a single culture vessel, g) providing a second media, which comprises a mixture of cytokines, wherein the mixture comprises at least one cytokine; thereby producing combined initiated CD4+ T cells and CD8+ T cells, h) transducing the combined initiated CD4+ T cells and CD8+ T cells with a vector, thereby producing genetically modified T cells; and i) harvesting the cells. In some alternatives, the at least one cytokine of step b) is IL-7, IL-15,or IL-21 or any combination thereof. In some alternatives, the IL-21, IL-15 and IL-7 are at a ratio of 10:5:1. In some alternatives, the at least one cytokine of step g) is IL-21, IL-15 or IL-7 or any combination thereof. In some alternatives, the IL-21, IL-15 and IL-7 are at a ratio of 2:0.2:1.

DETAILED DESCRIPTION

Figure 1:
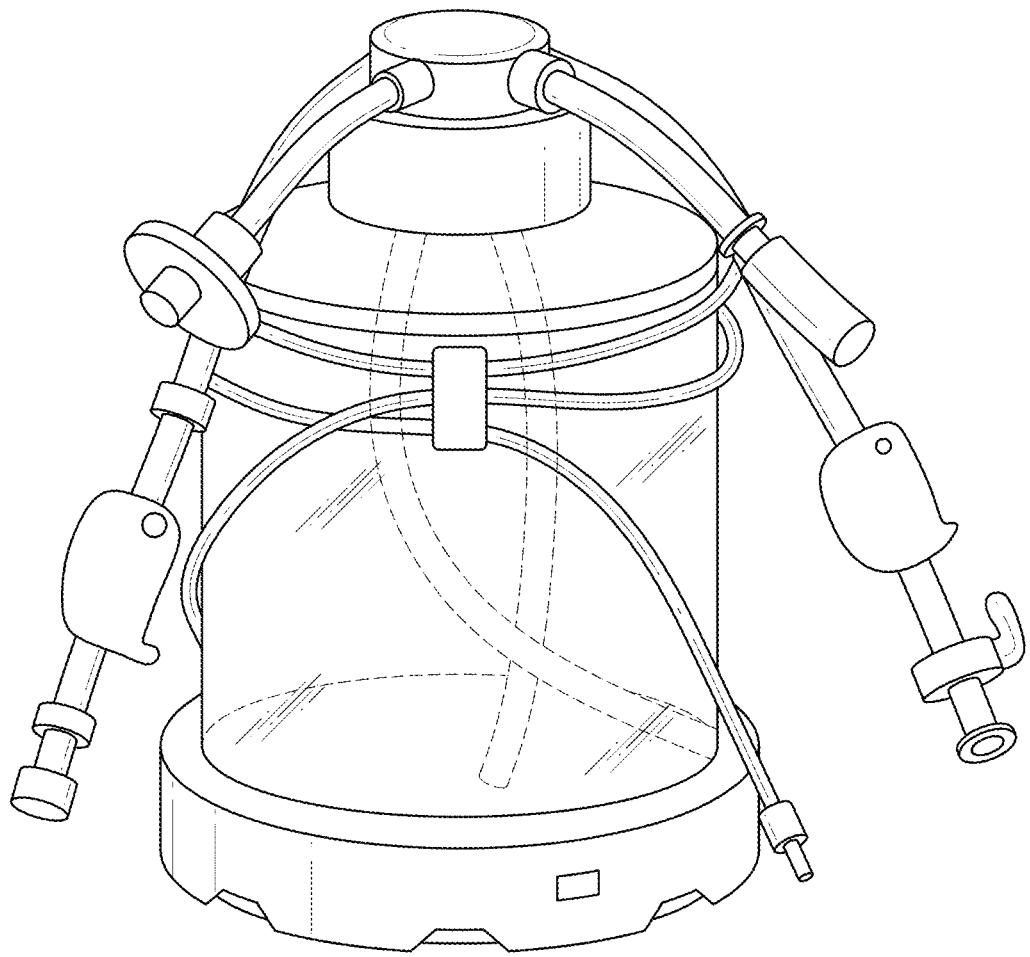
FIG. 1 shows a G-Rex100MCS vessel that may be used in some embodiments of the production of the genetically modified T cells.

Some embodiments provided herein relate to methods and compositions for making genetically modified T cells. In some such embodiments, CD4+ and CD8+ T cells are cultured in a single serum-free volume. In some embodiments, co-cultured CD4+ and CD8+ T cells are transduced with a lentiviral vector, and a population of transduced T cells are harvested within a shorter period of time as compared to conventional methods.

The current process of producing genetically modified cells for use in a therapy can be costly and it is estimated that commercially available products for producing these cells may be in the range of $20,000 to $40,000. The production of the cells is also difficult and labor intensive, which requires constant monitoring and feeding of cells under sterile conditions, as well as, the imprecise art of growing cells in commercially available cell culture bags (e.g. Gibco cell culture bags, Miltenyi Cell culture bags). The process of making the genetically modified cells may also be time consuming, in which the product is allowed to grow for about 14-21 days or longer with close monitoring, which may limit the number of simultaneous products being produced. Overall the process is a time consuming and labor intensive method for making the genetically modified cells for therapies. Some embodiments provided herein include processes having "open process steps" in which there is a single vector, or single patient per room and where there are biosafety cabinets (BSC; also known as biological safety cabinet) and centrifuges.

Some embodiments of the methods provided herein relate to efficient transduction and growth of transduced CD4 and CD8 T cells. In some embodiments, the transduced T cells contain a therapeutic payload, such as a chimeric antigen receptor. In some such embodiments, the population of T cells may be used in an autologous transfusion. In some embodiments, the growth of the transduced cells is sufficiently efficient to provide a population of transduced T cells in an amount sufficient for therapy of a subject within less than 10 day, 9 days, 8 days, 7, day, 6 days, 5 days, 4 days, or 3 days. In some embodiments, an amount sufficient for therapy of a subject can include a population of transduced CD4+ and CD8+ T cells from about 2 million cells to about 2 billion cells, from about 10 million cells to about 1 billion cells, from about 50 million cells to about 1 billion cells, from about 500 million cells to about 1 billion cells or an amount of cells within a range defined by any two of the aforementioned amounts. In some embodiments, CD4+ and CD8+ T cells from a subject are cultured in a single volume in a single vessel. In some embodiments, the growth medium is serum-free. In some embodiments, the growth medium is supplemented with at least one cytokine. In some embodiments, the growth medium is supplemented with IL-21, IL-15, and IL-7.

In some embodiments, genetically modified T cells, such as CD4 and CD8 T cells are prepared within a single vessel. In some alternatives, the process of manufacturing genetically modified T cells, such as CD4 and CD8 T cells within a single vessel may be performed in 3, 4, 5, 6, 7, 8, 9, 10, 11, 12, 13 or 14 days or for a time that is within a range of time defined by any two of the aforementioned time periods. Co-culturing the two cell types in the presence of a unique media allows the culture to be completed, preferably within seven days, in a single vessel, whereas using conventional techniques, culture needs to be performed for 14-21 days or more days (e.g., over a month) with the two subsets grown separately in two vessels. In situ transduction using the embodiments described herein is far more simple and rapid than conventional approaches and allows that the entire process is performed with minimal equipment and in a completely closed-system fashion.

Figure 2:
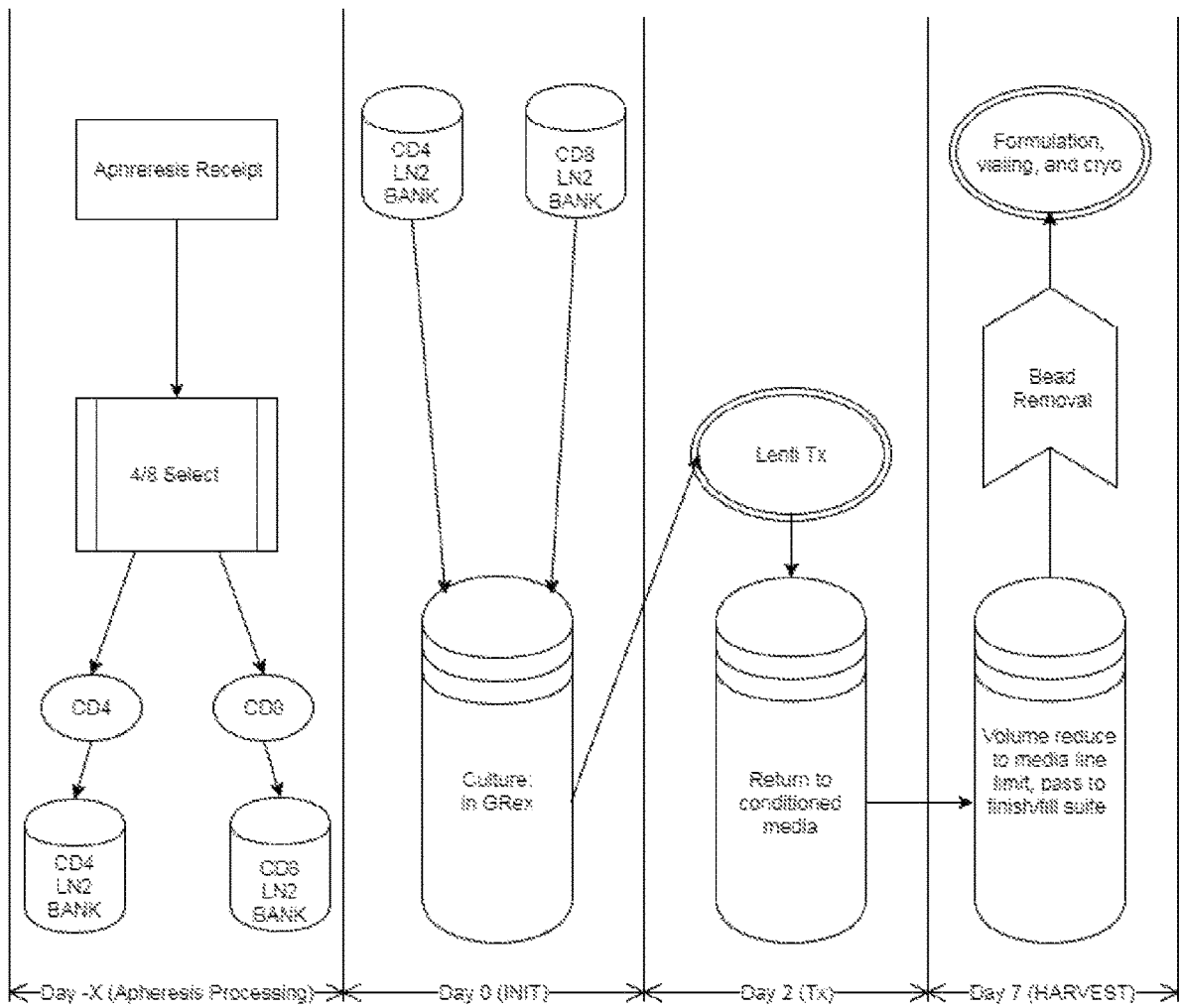
FIG. 2 depicts an exemplary embodiment of a process for preparing genetically modified T-cells.

An exemplary embodiment of a process or system for preparing genetically modified T cells from a subject is depicted in FIG. 2. As shown in FIG. 2, at Day X, a subject undergoes apheresis to obtain T cells, the CD4+ and CD8+

T cells are selected and sorted, and stored in liquid nitrogen banks. At Day 0, the stored T cells are initiated by culturing in a GRex vessel. At Day 2, the initiated cells are transduced with a lentiviral vector. At Day 7, the transduced cells are harvested, and can be stored.

Terms

Terms in the disclosure herein should be given their plain and ordinary meaning when read in light of the specification. One of skill in the art would understand the terms as used in view of the whole specification.

As used herein, "a" or "an" may mean one or more than one.

As used herein, the term "about" indicates that a value includes the inherent variation of error for the method being employed to determine a value, or the variation that exists among experiments.

As described herein, "genetically modify" and "genetically modified" have their plain and ordinary meaning when read in light of the specification, and may include but is not limited to, for example, a process for modifying an organism or a cell such as a bacterium, T-cell, bacterial cell, eukaryotic cell, insect, plant or mammal with genetic material, such as nucleic acid, that has been altered using genetic engineering techniques. For example, a nucleic acid such as DNA can be inserted in the host genome by first isolating and copying the genetic material of interest using molecular cloning methods to generate a DNA sequence, or by synthesizing the DNA, and then inserting this construct into the host organism. Genes can also be removed, or "knocked out", using a nuclease. Gene targeting is a different technique that uses homologous recombination to change an endogenous gene, and can be used to delete a gene, remove exons, add a gene, or introduce point mutations.

Genetic modification performed by transduction is described herein. "Transduction" refers to methods of transferring genetic material, such as, for example, DNA or RNA, to a cell by way of a vector. Common techniques use viral vectors, electroporation, and chemical reagents to increase cell permeability. The DNA can be transferred by a virus, or by a viral vector. Described herein are methods for modifying immune CD4+ and/or CD8+ T-cells. In order to achieve high expression of therapeutic genes and/or to increase the amount of chimeric antigen receptors on a cell surface, for example, T-cells are transduced with genetic material encoding a protein or a chimeric antigen receptor. T-cells can be genetically modified using a virus, for example. Viruses commonly used for gene therapy are adenovirus, adeno-associated virus (AAV), retroviruses or lentiviruses, for example.

Various transduction techniques have been developed, which utilize recombinant infectious virus particles for delivery of the nucleic acid encoding a chimeric antigen receptor. This represents a currently preferred approach to the transduction of T lymphocytes. As described herein, the viral vectors used for transduction can include virus vectors derived from simian virus 40, adenoviruses, adeno-associated virus (AAV), lentiviral vectors, or retroviruses. Thus, gene transfer and expression methods are numerous but essentially function to introduce and express genetic material in mammalian cells. Several of the above techniques can be used to transduce hematopoietic or lymphoid cells, including calcium phosphate transfection, protoplast fusion, electroporation, or infection with recombinant adenovirus, adeno-associated virus, lentivirus, or retrovirus vectors. Primary T lymphocytes have been successfully transduced by electroporation and by retroviral or lentiviral infection. As such, retroviral and lentiviral vectors provide a highly efficient approach for gene transfer to eukaryotic cells, such as T-cells. Moreover, retroviral or lentiviral integration takes place in a controlled fashion and results in the stable integration of one or a few copies of the new genetic information per cell. As described herein, the cells can be transduced in situ.

An "expression vector" or "vector" has their plain and ordinary meaning when read in light of the specification and may include but is not limited to, for example, a nucleic acid molecule encoding a gene that is expressed in a host-cell. Typically, an expression vector comprises a transcription promoter, a gene, and a transcription terminator. Gene expression is usually placed under the control of a promoter and such a gene is said to be "operably linked to" the promoter. Similarly, a regulatory element and a core promoter are operably linked if the regulatory element modulates the activity of the core promoter.

Viral vectors may have regulatory elements to provide expression of the heterologous nucleic acids in the cell. Vectors include but are not limited to plasmid, minicircles, yeast, and viral genomes. In some alternatives, the vectors are plasmid, minicircles, viral vectors, DNA or mRNA. In some alternatives, the vector is a lentiviral vector or a retroviral vector. In some alternatives, the vector is a lentiviral vector.

"Spinoculation" has its plain and ordinary meaning when read in light of the specification, and may include but is not limited to, for example, centrifugal inoculation (of cell cultures).

"Media" has its plain and ordinary meaning when read in light of the specification, and may include but is not limited to, for example, solid or liquid or semi-solid designed to support the growth of microorganisms or cells. Different types of media are used for growing different types of cells and, in some contexts, may be referred to as a base media. In some alternatives herein, media is supplemented to support growth of CD4 and CD8 containing cells in a single vessel, such as a G-Rex100MCS (FIG. 1). Base media can include a commercial product, for example, XVIVO-15 (supplied by Lonza) or PRIME-XV (supplied by Irvine Scientific). The single vessel may be gas-permeable, and may include a flexible culture substrate. For such vessels there is virtually an unlimited nutrient/waste reservoir. The vessel has a textured support, which generates high reproducibility of culture surface. The system is completely closed-system compatible. Desirably, there is virtually no culture maintenance, in which many processing steps can be performed in-vessel, minimizing gross manipulations. Additionally, more than 2 billion cells may be generated in one week, leaving a smaller waste footprint than culture bags.

"Biosafety cabinet," (BSC) has its plain and ordinary meaning when read in light of the specification and may include but is not limited to, for example, an enclosed, ventilated laboratory workspace for safely working with materials contaminated with (or potentially contaminated with pathogens requiring a defined biosafety level. Several different types of BSC exist, differentiated by the degree of biocontainment required. Protocols for working in a BSC are known to those of skill in the art and are available commercially (e.g. Thermo Scientific biological safety cabinets).

"Protein supplement" has its plain and ordinary meaning when read in light of the specification and may include but is not limited to, for example, commercially available proteins mixtures for adding to a media for cell growth. Protein supplements may be supplied by commercial companies, such as Knockout-SR (supplied by ThermoFisher Scientific) or fetal bovine serum.

"Nuclease" or "endonuclease" has their plain and ordinary meaning when read in light of the specification, and may include but is not limited to, for example, an enzyme configured to cleave the phosphodiester bonds between the nucleotide subunits of nucleic acids. In some alternatives a polynucleotide encoding a nuclease is provided to a cell for genetic modification of the cell. Without being limiting, examples of endonucleases can include for example, a CRISPR enzyme or a restriction endonuclease. In some alternatives herein, cells may be genetically modified by a nuclease prior to transduction with a viral vector.

A "restriction enzyme" or "restriction endonuclease" has their plain and ordinary meaning when read in light of the specification, and may include but is not limited to, for example, an enzyme that recognizes and binds DNA at or near specific recognition nucleotide sequences so that it can cut at a restriction cleavage sites. In some alternatives the endonuclease recognition site is specific for a restriction endonuclease.

"Transcription activator-like effector nucleases" (TALENS) has its plain and ordinary meaning when read in light of the specification and may include but is not limited to, for example, artificial restriction enzymes generated by fusing a Tal effector DNA binding domain to a DNA cleavage domain. Tal effectors are bacterial DNA-binding proteins consisting of highly homologous 34 amino-acid modules that can bind one nucleotide with high affinity. The variable twelfth and thirteenth amino acids of the TALENS module, referred to as repeat-variable di-nucleotide, confers base specificity (e.g., NN→G/A, NI→A, NG→T, NK→G, HD→C, and NS→A/T/C/G) and TALEN arrays that target a desired nucleotide sequence can be generated by assembling the individual modules. The relationship between the amino acid sequence and the DNA recognition element has allowed the engineering of specific DNA binding domains by the selection of a combination of repeat segments contacting the correlating Repeat Variable Diresidue (RVDs). TALENS can be used to edit genomes by inducing double-strand breaks (DSBs) in cells of interest, wherein the cells respond by invoking several types of repair mechanisms.

"Zinc finger proteins" (ZFP) has their plain and ordinary meaning when read in light of the specification, and may include but is not limited to, for example, eukaryotic DNA binding proteins. The most common ZFP motifs for genome editing, for example, are the Cys2-His2 fingers, and each type are specific for a nucleotide triplet. Artificial ZFP domains can be generated to target specific DNA sequences that are usually 9-18 nt long by the assembly of individual zinc fingers. The term "Designer zinc finger proteins," refers to zinc finger proteins with purposefully re-engineered DNA-binding specificities that can provide a broadly applicable technology for targeting functional domains to almost any gene of interest in many types of cells. Zinc finger nucleases (ZFNs) are a powerful tool for performing targeted genomic manipulation in a variety of cell types in humans. ZFNs consist of an engineered DNA-binding zinc finger domain linked to a non-specific endonuclease domain and can introduce double-stranded breaks (DSBs) that stimulate both homologous and non-homologous recombination, which can then be harnessed to perform genomic manipulation. As such, ZFPs have potential in both research and gene therapy applications.

Clustered Regularly Interspaced Short Palindromic Repeats (CRISPR) has their plain and ordinary meaning when read in light of the specification, and may include but is not limited to, for example, a DNA loci that can contain short repetitions of base sequences, in which each repetition is followed by short segments of spacer DNA from viral exposure. The CRISPR regions can be associated with cas genes that code for proteins related to CRISPRs. The CRISPR/Cas system is a prokaryotic immune system that confers resistance to foreign genetic elements, such as plasmids and phages and provides a form of acquired immunity. CRISPR spacers recognize and cut these exogenous genetic elements in a manner analogous to RNAi in eukaryotic organisms. As a genome editing mechanism, an RNA guided endonuclease, a Cas protein, and appropriate guide RNA can be delivered into a cell and the organisms' genome can be cut at a desired location. CRISPRS are an efficient mechanism for targeting/modifying genes.

"MegaTal" nuclease has its plain and ordinary meaning when read in light of the specification and may include but is not limited to, for example, a hybrid nuclease architecture, which combines the engineerability of a TAL effector with the cleavage sequence specificity of a meganuclease (mn) cleavage domain. The architecture of the MegaTal allows the generation of active and specific nucleases that are compatible with viral and non-viral cell delivery methods.

"Chimeric Antigen Receptor" (CAR) has its plain and ordinary meaning when read in light of the specification and may include but is not limited to, a chimeric T-cell receptor, an artificial T-cell receptor or a genetically engineered receptor. These receptors can be used to graft the specificity of a monoclonal antibody or a binding portion thereof onto a desired cell (e.g., a T-cell). Often, the transfer of the coding sequence for the CAR to a recipient cell is accomplished using a retroviral vector. The structure of the CAR can comprise single-chain variable fragments (scFv) derived from monoclonal antibodies, fused to CD3-zeta transmembrane and endodomain. Such molecules result in the transmission of a zeta signal in response to recognition by the scFv of its target.

"CD19" has its plain and ordinary meaning when read in light of the specification, and may include but is not limited to, a protein that is found on the surface of white blood cells and can assemble with the antigen receptor of B lymphocytes in order to decrease the threshold for antigen receptor-dependent stimulation. CD19 is expressed on follicular dendritic cells and B cells. CD19 is present on B cells from earliest recognizable B-lineage cells during development to B-cell blasts but is lost on maturation to plasma cells. CD19 primarily acts as a B cell co-receptor in conjunction with CD21 and CD81. Upon activation, the cytoplasmic tail of CD19 becomes phosphorylated, which leads to binding by Src-family kinases and recruitment of PI-3 kinase. As on T-cells, several surface molecules form the antigen receptor and form a complex on B lymphocytes.

As a whole, the alternative methods for making genetically modified cells described herein desirably allow for all steps to be performed in a completely closed system, which permits this process to be performed to make products for multiple patients, using multiple viral constructs (e.g. lentiviral constructs), in the same space at the same time with no additional physical separation beyond the cultureware and tubing harnesses necessary for the execution of the process. This has major implications for facility and workflow design, allowing much higher efficiency usage of manufacturing floor space and staff.

Such methods may be used to generate chimeric antigen bearing (CAR) T cells by viral transduction. The cells may also be subjected to other manipulations or genetic modifications in the embodied systems described herein and, preferably may be modified by lentivirus, adeno-associated virus, adenovirus or retrovirus.

Certain Methods of Preparing Genetically Modified T Cells

In some alternatives, a method of manufacturing genetically modified T cells, wherein the genetically modified T cells comprise a chimeric antigen receptor is provided, the method comprising: providing CD8+ T cells and CD4+ T cells in a first media in a single culture vessel; placing a second media into the single culture vessel, thereby producing co-cultured CD4+ T cells and CD8+ T cells, which are initiated for transduction; harvesting the initiated CD4+ T cells and CD8+ T cells; and transducing the initiated CD4+ T cells and CD8+ T cells with a vector, thereby producing genetically modified T cells. In some alternatives, the method is performed in a biological safety cabinet (BSC). In some alternatives, the method is performed outside of a biological safety cabinet (BSC). In some alternatives, the vector is a viral vector. In some alternatives, the vector is a lentiviral vector, an adeno-associated vector, or an adenoviral vector. In some alternatives, the transduction is performed by magnetically concentrating the initiated CD4+ T cells and CD8+ T cells, for example on CTS Dynabeads CD3/CD28 and incubating a transduction mixture with the initiated CD4+ T cells and CD8+ T cells for a defined period. In some alternatives, the culture media is removed from the culture vessel prior to adding the transduction media to the cells. In some alternatives, the defined period is in a range from about 1 hour to about 24 hours, from about 2 hours to about 12 hours, or from about 2 hours to about 5 hours. In some alternatives, the removed culture media is re-introduced into the vessel at the end of the defined period. In some alternatives, the transduction mixture comprises the vector. In some alternatives, the first media is a cytokine free media. In some alternatives, the second media comprises at least one cytokine. In some alternatives, the at least one cytokine is IL-2, IL-7, IL-15, or IL-21 or any combination thereof. In some alternatives, the at least one cytokine is IL-21, IL-15, and IL-7. In some alternatives, the transducing step is performed 24 hours after the harvesting step of the initiated CD4+ T cells and CD8+ T cells. In some alternatives, the first and or second media further comprises a protein supplement. In some alternatives, the transduction mixture further comprises protamine sulfate or polybrene or both. In some alternatives, the transduction mixture further comprises an interleukin. In some alternatives, the transduction mixture comprises IL-2, IL-21, IL-15 or IL-7 o rany combination thereof. In some alternatives, the genetically modified CD4+ T cells and CD8+ T cells are harvested 3, 4, 5, 6, 7, 8, 9, 10, 11, 12, 13, or 14 days after the transducing step or any number of days within a range defined by any two aforementioned time periods. In some alternatives, the vector comprises a nucleic acid encoding a protein for therapy. In some alternatives, the protein for therapy comprises cytokines, chimeric cytokine/costimulatory proteins, or pro- or anti-inflammatory proteins. In some alternatives, the vector comprises a nucleic acid encoding a chimeric antigen receptor. In some alternatives, the initiated CD4+ T cells and CD8+ T cells are further modified with a nuclease. In some alternatives, the nuclease is a zinc finger nucleases (ZFNs), Transcription Activator-like Effector Nucleases (TALENs), the CRISPR/Cas system, RNA guided endonucleases or engineered meganuclease re-engineered homing endonucleases. In some alternatives, the chimeric antigen receptor comprises a signal peptide, an antigen-binding domain, a transmembrane domain, a co-stimulatory domain, and an intracellular domain of a T-cell receptor. In some alternatives, the genetically modified T cells express a chimeric antigen receptor (CAR), such as a CAR specific for binding or interaction with CD19. In some alternatives, the vector further comprises a second nucleic acid encoding a genetic tag. In some alternatives, the genetic tag is EGFRt. In some alternatives, the process of manufacturing genetically modified T cells, such as CD4 and CD8 T cells within a single vessel may be performed in 3, 4, 5, 6, 7, 8, 9, 10, 11, 12, 13 or 14 days or for a time that is within a range of time defined by any two of the aforementioned time periods. In some alternatives, the at least one cytokine is IL-7, IL-15, or IL-21 or any combination thereof. In some alternatives, the at least one cytokine is IL-2, IL-7, IL-15, and IL-21.

In some alternatives, a method of manufacturing genetically modified T cells is provided, wherein the genetically modified T cells comprise a chimeric antigen receptor, the method comprising: a) providing CD8+ T cells and CD4+ T cells within two separate fractions of a first media, b) providing at least one cytokine into the separate fractions of first media, wherein the separate fractions comprises CD8+ T cells in a first fraction and CD4 T cells in a second fraction; c) combining the first fraction and second fraction containing the CD8+ T cells and CD4+ T cells, thereby producing a combined cell fraction; d) providing magnetic beads, such as Dynabeads (e.g., CTS Dynabeads CD3/CD28) to the combined cell fraction and magnetically concentrating the CD4+ T cells and CD8+ T cells; e) removing the magnetic beads e.g., Dynabeads; f) adding the combined cell fraction comprising the CD4+ and CD8+ cells into a single culture vessel; g) providing a second media, which comprises a mixture of cytokines, wherein the mixture comprises at least one cytokine; thereby producing combined initiated CD4+ T cells and CD8+ T cells; h) transducing the combined initiated CD4+ T cells and CD8+ T cells with a vector, thereby producing genetically modified T cells; and i) harvesting the cells. In some alternatives, the at least one cytokine of step b) is IL-7, IL-15, and IL-21. In some alternatives, the IL-21, IL-15 and IL-7 are at a ratio of 10:5:1. In some alternatives, the at least one cytokine of step g) is IL-21, IL-15 and IL-7. In some alternatives, the IL-21, IL-15 and IL-7 are at a ratio of 2:0.2:1. In some alternatives, the method is performed in a biological safety cabinet (BSC). In some alternatives, the method is performed outside of a biological safety cabinet (BSC). In some alternatives, the vector is a viral vector. In some alternatives, the vector is a lentiviral vector, an adeno-associated vector, or an adenoviral vector. In some alternatives, the transduction is performed by magnetically concentrating the initiated CD4+ T cells and CD8+ T cells, for example on CTS Dynabeads CD3/CD28 and incubating a transduction mixture with the initiated CD4+ T cells and CD8+ T cells for a defined period. In some alternatives, the transduction mixture comprises the vector. In some alternatives, the transducing step is performed 24 hours after the harvesting step of the initiated CD4+ T cells and CD8+ T cells. In some alternatives, the transduction mixture further comprises protamine sulfate or polybrene or both. In some alternatives, the transduction mixture further comprises an interleukin. In some alternatives, the transduction mixture comprises IL-2, IL-21, IL-15 and/or IL-7. In some alternatives, the genetically modified CD4+ T cells and CD8+ T cells are harvested 3, 4, 5, 6, 7, 8, 9, 10, 11, 12, 13, or 14 days after the transducing step or any number of days within a range defined by any two aforementioned time periods. In some alternatives, the vector comprises a nucleic acid encoding a protein for therapy. In some alternatives, the protein for therapy comprises cytokines, chimeric cytokine/costimulatory proteins, or proor anti-inflammatory proteins. In some alternatives, the vector comprises a nucleic acid encoding a chimeric antigen receptor. In some alternatives, the initiated CD4+ T cells and CD8+ T cells are further modified with a nuclease. In some alternatives, the nuclease is a zinc finger nucleases (ZFNs), Transcription Activator-like Effector Nucleases (TALENs), the CRISPR/Cas system, RNA guided endonucleases or engineered meganuclease re-engineered homing endonucleases. In some alternatives, the chimeric antigen receptor comprises a signal peptide, an antigen-binding domain, a transmembrane domain, a co-stimulatory domain, and/or an intracellular domain of a T-cell receptor. In some alternatives, the genetically modified T cells express a chimeric antigen receptor (CAR). In some alternatives, the vector further comprises a second nucleic acid encoding a genetic tag. In some alternatives, the genetic tag is EGFRt. In some alternatives, the process of manufacturing genetically modified T cells, such as CD4 and CD8 T cells within a single vessel may be performed in 3, 4, 5, 6, 7, 8, 9, 10, 11, 12, 13 or 14 days or for a time that is within a range of time defined by any two of the aforementioned time periods.

EXAMPLES

Example 1

A Single-Train Process in a Single Vessel

An exemplary protocol for performing a single train process in a single vessel is provided in TABLE 1.

TABLE 1

| Stage (time) | Steps |
|---|---|
| Initiation: (Day 0) | 1. Make 1.2 L supplemented media (SM).<br>  a. Thaw a 25 ml aliquot of Knockout (KO) Serum Replacement media (Thermo Fisher Scientific, San Diego CA) in a 37° C. dry heating block, inverting frequently.<br>  b. Remove 24 ml XVIVO-15 media (Lonza BioWhittaker) from a 1 L bottle, and add 24 ml of the aliquot to the 1 L bottle of XVIVO-15 media.<br>  c. Into a 50 ml conical tube, draw 40 ml XVIVO + KO and add to it 1 ml IL-21, 100 µl IL-15, and 500 µl IL-7 (all 10 ng/µl stocks).<br>2. Pipette 48 ml SM into each of two 50 mL conical tubes.<br>3. Thaw two 50e6 cell vials of both CD8 and CD4 isolated primary T-cells, transferring the vials of cells to the appropriately labeled 50 mL conical tubes.<br>4. Centrifuge for 10 min at 400 g, aspirate supernatant carefully.<br>5. While centrifuge is running, assemble a Jensen cap (a Jensen cap allows access to a vessel's contents, such as a media bottle, without opening the vessel; the cap includes an opening with an air filter, and an opening with tubing that enters the vessel and extends out of the vessel) with tubing extension on the 1 L XVIVO media bottle and pump 980 mL SM into a G-Rex100MCS (Wilson Wolf, Saint Paul, MN). Place in incubator until Step 11.<br>6. Resuspend CD4 cells in a final volume of 10 ml, and remove a counting sample.<br>7. Resuspend CD8 cells in a final volume of 10 ml, and remove a counting sample. |

TABLE 1-continued

| Stage (time) | Steps |
|---|---|
| | 8. Count cells.<br>9. Determine volumes necessary for 62.5e6 of each cell type.<br>10. When volume of cell suspension for the G-Rex has been determined, add 0.9375 ml CTS Dynabeads with antibodies attached against CD3 and CD28 to activate the cells (Thermo Fisher Scientific, San Diego CA) to a 50 ml conical tube containing 30 ml media, and wash beads on the CTS magnet (Dynamag; Thermo Fisher Scientific, San Diego CA).<br>11. Remove beads from magnet, add appropriate volumes of cell suspension to the bead tube, and add media to the tube to a total volume of 30 ml. There should now be a 30 ml cell suspension at ~4.2e6 cells/ml in a single 50 ml conical tube. Exchange the cap of the 50 ml conical tube with a Burton tube cap (similar to Jensen cap for a 50 ml conical tube) with attached PAC-03 and rapidly transfer the cell/bead mixture to the filled G-Rex100MCS. |
| Transduction: (Day +1) | 1. Remove the G-Rex100MCS from the incubator. Replace CLAVE connection on shortest port with a tubing extension. Gently place the G-Rex100MCS on the CTS magnet and transfer media to a TP1000 (transfer pack, 1000 ml) via the cells line. Place excess media in a 37° C. incubator.<br>2. Remove a vial of lentiviral vector from the −80° C. freezer and defrost on the benchtop.<br>3. Prepare 25 ml transduction (Tx) Mix in a Burton tube by combining the following:<br>  a. 25 mL media<br>  b. 300 µl protamine sulfate<br>  c. 100 µl vector<br>  d. 1X cytokine final concentration (25 µl IL-21, 2.5 µl IL-15, and 12.5 µl IL-7).<br>4. Using a PAC-03, transfer the Tx mix to the G-Rex100MCS still located on the CTS magnet.<br>5. Gently transfer the G-Rex100MCS to a 37° C. 5% CO$_2$ incubator, incubate for 4 hours.<br>6. Following incubation, replace media in G-Rex100MCS from the TP1000 via the shortest tubing extension. When ~100 ml of media has been transferred to the G-Rex100MCS, swirl gently to resuspend detached cells to encourage even distribution following volume-up. |
| Harvest: (Day +7) | 1. Remove G-Rex100MCS from the incubator with minimal agitation. Using the media line, transfer as much media as possible to a TP1000.<br>2. Swirl G-Rex100MCS sufficiently to dislodge all cells from the bottom. Transfer cells via the 'cells' line to a TP600 labeled "cells". Rinse the G-Rex100MCS by gravity draining ~50 ml media back into the G-Rex100MCS and transferring into the cells bag. Agitate bag to dislodge remaining beads from cells.<br>3. Weld a tared Hamlett tube to the cells bag, label it "Bead removed cells". Clamp the line, place the cells bag on the CTS magnet, close the lid, and incubate 2 minutes.<br>4. Tilt the magnet to 45° and remove the clamp to drain the cells into the Hamlett tube. Volume the Hamlett tube to 500 mL using media from the TP1000 |

TABLE 1-continued

| Stage (time) | Steps |
|---|---|
| | used in step 1, mix well, and remove a 1 mL count/flow staining sample.<br>5. Spin cells at 400 g × 15 min.<br>6. Count cells using the NC3000 counter and set aside a flow staining sample.<br>7. Prepare sufficient labeled cryovials to accommodate the generated cells at 100e6/ml.<br>8. Resuspend cells in Cryostor CS5 freeze media (BioLife Solutions) to a density of 100e6/ml and transfer to prepared vials.<br>9. Freeze vials overnight at −80° C. in a freezermate, then transfer to liquid nitrogen for long-term storage. |

Example 2

A Single-Train Process in a Single Vessel

An example protocol for performing a single train process in a single vessel is provided in TABLE 2.

TABLE 2

| Stage (time) | Steps |
|---|---|
| Initiation:<br>(Day 0) | 1. Make 200 mL supplemented media (SM).<br>   a. Thaw a 5 ml aliquot of Knockout serum replacement (KSR) media in a 37° C. dry heating block, inverting frequently.<br>   b. To 196 mL XVIVO-15 media, add 4 ml of the KSR, and 200 μL IL-21, 20 μL IL-15, and 100 μL IL-7 (all 10 ng/ul stocks).<br>2. Pipette 48 ml SM into each of two 50 mL conical tubes.<br>3. Thaw two 50e6 cell vials of both CD8 and CD4 isolated primary T-cells, transferring the vials of cells to the appropriately labeled 50 mL conical tubes.<br>4. Centrifuge for 10 min at 400 g, aspirate supernatant carefully.<br>5. Resuspend CD4 cells in a final volume of 10 ml SM, and remove a counting sample.<br>6. Resuspend CD8 cells in a final volume of 10 ml SM, and remove a counting sample.<br>7. Determine volumes necessary for a 62.5e6 of each cell type.<br>8. When volume of cell suspension for the G-Rex has been determined, add 0.9375 ml CTS Dynabeads with antibodies attached against CD3 and CD28 to activate the cells (Thermo Fisher Scientific, San Diego CA) to a 50 ml conical tube containing 30 ml media, and wash beads on the CTS magnet (Dynamag; Thermo Fisher Scientific, San Diego CA).<br>9. Remove the bead tube from the magnet and add the appropriate volumes of cell suspension to the tube to resuspend the beads. Add SM to the cell/bead mixture to a final volume of 40 mL, and transfer the cells to a VueLife bag as quickly as possible. Fill the remaining working volume of the VueLife bag with SM, mix by rocking, and place in a 37° C. CO₂ incubator. |
| Transduction:<br>(Day +1) | 1. Remove a vial of lentiviral vector from the −80° C. freezer and defrost on the benchtop.<br>2. Prepare 25 mL transduction (Tx) Mix in a Burton tube by combining the following:<br>   a. 25 mL media<br>   b. 300 μl protamine sulfate<br>   c. 100 μl vector<br>   d. 1X cytokine final concentration (25 μl IL-21, 2.5 μl IL-15, and 12.5 μl IL-7).<br>3. Placing the VueLife bag on a Dynamag CTS or similar magnet, drain media from the VueLife bag into a secondary container such as a Transfer Pack or Jensen Tube.<br>4. Add the Tx Mix from Step 2 to the VueLife bag. Disconnect all lines from the bag and place in a 37° C. incubator for 3 hours.<br>5. During the 3 hour incubation, make 900 mL complete X-VIVO 15 media and transfer 875 mL to a G-Rex100MCS.<br>6. Following the 3 hour incubation, transfer the cell/bead/TxMix mixture to the G-Rex100MCS containing media. Rinse the VueLife bag with the leftover media set aside prior to transduction into the G-Rex.<br>7. Seal the G-Rex and place in a 37° C. CO₂ incubator. |
| Harvest:<br>(Day +7) | As Example 1. |

Example 3

Single Train Process in a Single Vessel Compared to Conventional Process

A single train process in a single vessel was performed in a method substantially similar to the process described in Example 1. TABLE 3 compares the single train process in a single vessel (84121) with a conventional method used in a PLAT-02 clinical trial, for preparing genetically modified T cells. In the PLAT-02 methods, cells were cultured in bags with media containing fetal bovine serum (FBS), and the CD4 and CD8 populations were cultured separately.

TABLE 3

| Parameter: | 84121 method (7 day process for production of genetically modified cells) | PLAT-02 method (conventional protocol for production of genetically modified cell) |
|---|---|---|
| CD4+/CD8+ culture: | CD4 and CD8 T cells grown together in G-Rex. | CD4 and CD8 T cells grown separately in VueLife bags. |
| Culture time: | 7 days. | More than 14 days. |
| Handling time: | 30 hours, hands-on. | About 130 hours, frequent handling. |
| Volume adjustments to culture medium: | No counting during incubations, media volume remains constant. | Aliquots taken for frequent counting, media volume adjustments required. |

With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those of skill within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., " a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., " a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

Any of the features of an embodiment of the first aspect to the second aspect is applicable to all aspects and embodiments identified herein. Moreover, any of the features of an embodiment of the first aspect or the second aspect is independently combinable, partly or wholly with other embodiments described herein in any way, e.g., one, two, or three or more embodiments may be combinable in whole or in part.

What is claimed is:

1. A method of manufacturing genetically modified T cells, wherein the genetically modified T cells comprise a chimeric antigen receptor (CAR), the method comprising:
   (a) providing CD8+ T cells and CD4+ T cells in a culture media in a single culture vessel, wherein the culture media comprises IL-7, IL-15, and IL-21, and lacks serum, thereby obtaining co-cultured T cells;
   (b) initiating the CD8+ T cells and CD4+ T cells for transduction, thereby obtaining initiated T cells, wherein the initiation is performed for a period within a range from about 12 hours to about 24 hours;
   (c) transducing the initiated T cells with a vector encoding the CAR, thereby obtaining transduced T cells, wherein the transducing comprises:
      (i) magnetically concentrating the initiated T cells, thereby obtaining concentrated T cells, and
      (ii) incubating the concentrated T cells with a transduction media for 4 hours or less; and
   (d) measuring an amount of the transduced T cells, wherein the amount is at least sufficient for a therapeutic dose of the transduced T cells in an adoptive cell transfer to a human subject, and harvesting the transduced T cells, thereby obtaining the genetically modified T cells, wherein step (d) is performed less than 7 days or less after step (b) is performed.

2. The method of claim 1, wherein step (b) comprises contacting the co-cultured T cells with magnetic beads coated with an anti-CD3 antibody and an anti-CD28 antibody antibodies or antigen binding fragments thereof.

3. The method of claim 1, wherein step (i) further comprises removing the culture media from the vessel to obtain removed culture media.

4. The method of claim 3, further comprising (iii) reintroducing the removed culture media into the vessel after the 4 hours or less.

5. The method of claim 1, wherein the transduction media comprises a component selected from protamine sulfate, polybrene, an interleukin, or any combination thereof.

6. The method of claim 1, wherein the transduction media comprises protamine sulfate, Il-7, IL-15, IL-21, and the vector.

7. The method of claim 1, wherein step (d) comprises cryofreezing the genetically modified T cells.

8. The method of claim 1, wherein the method is performed outside of a biological safety cabinet (BSC).

9. The method of claim 1, wherein the vector is a viral vector selected from a lentiviral vector, an adeno-associated vector, or an adenoviral vector.

10. The method of claim 1, wherein the vector further comprises a nucleic acid encoding a genetic tag, or a protein for therapy.

11. The method of claim 1, wherein the CD4+ T cells and CD8+ T cells are obtained from a single subject.

12. The method of claim 1, wherein step (d) is performed 6 days after step (b) is performed.

* * * * *